United States Patent [19]

Columbus

[11] Patent Number: 4,473,457

[45] Date of Patent: Sep. 25, 1984

[54] LIQUID TRANSPORT DEVICE PROVIDING DIVERSION OF CAPILLARY FLOW INTO A NON-VENTED SECOND ZONE

[75] Inventor: Richard L. Columbus, Rochester, N.Y.

[73] Assignee: Eastman Kodak Company, Rochester, N.Y.

[21] Appl. No.: 362,930

[22] Filed: Mar. 29, 1982

[51] Int. Cl.³ .................. G01N 1/00; G01N 27/46; G01N 33/84
[52] U.S. Cl. .................. 204/416; 73/864.91; 204/409; 422/100
[58] Field of Search .................. 204/409, 416; 73/864.91; 422/55, 58, 100, 102; 356/246

[56] References Cited

U.S. PATENT DOCUMENTS

| 4,233,029 | 11/1980 | Columbus | 422/100 X |
| 4,254,083 | 3/1981 | Columbus | 422/100 X |
| 4,271,119 | 6/1981 | Columbus | 422/100 X |
| 4,273,639 | 6/1981 | Gottermeier | 204/116 |

Primary Examiner—Arnold Turk
Attorney, Agent, or Firm—Dana M. Schmidt

[57] ABSTRACT

Diverting apertures are operative to divert capillary transport of liquid from one transport zone into a second, unvented zone before the diverting aperture is surrounded by liquid flow in the first zone, by providing structure such that (a) the height of the head of liquid that is above the aperture, is selected to be sufficiently large, compared to the distance that the diverted liquid must flow into the second zone, and (b) the width of the first zone, and the dimension of the diverting aperture parallel thereto, have a predetermined relation.

12 Claims, 5 Drawing Figures

LIQUID TRANSPORT DEVICE PROVIDING DIVERSION OF CAPILLARY FLOW INTO A NON-VENTED SECOND ZONE

FIELD OF THE INVENTION

This invention relates to a device for transporting liquid into different zones by capillary attraction.

BACKGROUND OF THE INVENTION

My U.S. Pat. No. 4,271,119, issued June 2, 1981, is directed to a liquid transport device which, by means of a downstream diverting aperture in a wall member of a first capillary zone, provides capillary flow into a second capillary zone extending from that wall member. Because of the shape of the diverting aperture, liquid is diverted into the second zone from the first zone before the liquid flow of the first zone completely surrounds the diverting apertures. Failure to achieve flow into the second zone before the aperture is surrounded produces air entrapment, so that subsequent flow into the second zone is prevented.

Such a device has provided very successful diversion of capillary flow of liquid into the noted second zone, and has proved to be highly useful as an ion bridge for potentiometric test elements containing ISE's.

Notwithstanding the success of that device, there remained some aspects for improvement. For diverting apertures having a transverse flow-through area greater than about 0.2 mm$^2$, the shape of the diverting aperture was critical—the aperture had to be considerably longer than wide, that is, with a length to width ratio of preferably between about 2.5 and about 10.0. In other words, the width dimension was no greater than 0.4 that of the length dimension. Such width-to-length relationships excluded circularly shaped apertures.

It would be advantageous to provide such a device wherein the diverting aperture is both circular in shape and has a flow-through area greater than about 0.2 mm$^2$. Such circular apertures are the simplest to manufacture.

SUMMARY OF THE INVENTION

I have discovered that the sought-for improvements are available in a device of the type described, wherein a second capillary zone extends from a first capillary zone, and diverting aperture means are provided to divert some of the liquid from the first zone to the second zone, if certain conditions are met, viz: the height of the liquid at the diverting aperture is manipulated to be predeterminedly large compared to the distance the liquid must flow in the second zone, and the flow-through width of the first zone at the diverting aperture is constructed within a predetermined size range with respect to the dimension of the diverting aperture that parallels the first zone flow-through width dimension.

More specifically, there is provided a liquid transport device comprising means providing first and second capillary transport zones. The first zone has liquid access means and is formed by a first set of opposed surfaces spaced to provide capillary flow, and means defining a flow-through width of the first zone. The second zone means includes diverting aperture means in one of said opposing surfaces forming the first zone to divert a portion of the capillary flow into the second zone and form a first end of the second zone. A terminating surface is disposed at the end of the second zone opposite the diverting aperture. The diverting aperture means is located downstream from said access means and is constructed to provide the following flow-through characteristics: a width dimension that is greater than 0.4 of its length dimension, and a flow-through area greater than about 0.2 mm$^2$. Two parameters of the device, viz, (1) the ratio between flow-through width of the first zone and the aperture dimension that extends parallel to the flow-through width, and (2) the spacing between the members of the first zone at the diverting aperture means, compared to the distance of liquid travel in the second zone, are selected so that the liquid flowing in the first zone enters the diverting aperture and contacts the terminating surface, before the flow of the liquid in the first zone surrounds the diverting aperture means.

Thus, it is an advantage of the present invention that capillary flow is successfully diverted from a first zone so as to flow the length of a second zone, without the need for an air vent in the second zone.

It is a further advantage of the invention that such flow is achieved using apertures of many shapes, including circular apertures.

Other features and advantages will become apparent upon reference to the following Description of the Preferred Embodiments, when read in light of the attached drawings.

DESCRIPTION OF THE PREFERRED EMBODIMENTS

Figure 1:
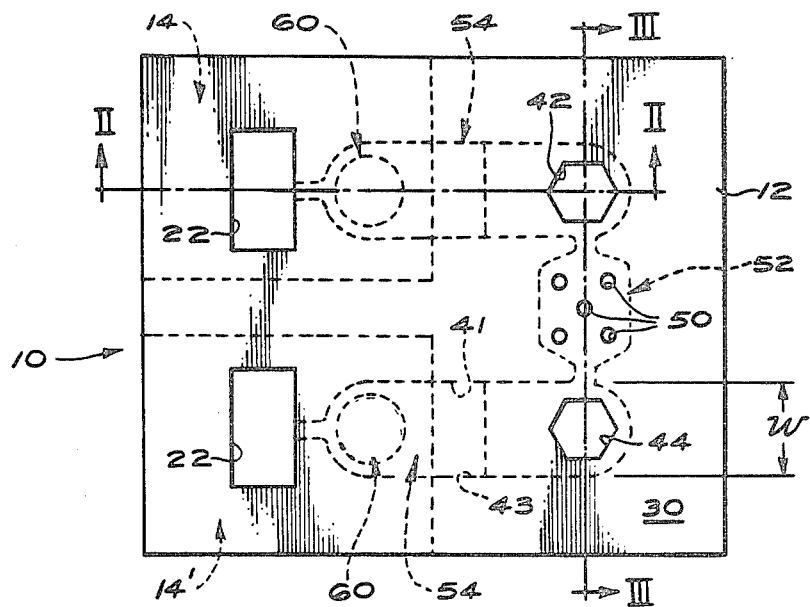
FIG. 1 is a plan view of a device constructed in accordance with the invention.

The preferred embodiments hereinafter described refer particularly to the use of the invention in an element for the potentiometric detection of ionic analytes. In such an element, an ion-selective electrode is the terminating surface for the second zone. In addition, the invention is useful regardless of the end process that is applied to the liquid, wherein other kinds of terminating surfaces close off the second zone.

The ionic analytes, commonly called electrolytes, detectable in the preferred embodiment are those present in any liquid, whether biological or industrial. The device of the invention works particularly well for biological liquids such as serum, urine and spinal fluid having surface tensions between about 25 and about 75 dynes/cm.

The device 10 shown in FIG. 1 comprises an electrically insulative frame 12 which mounts a spaced-apart pair of preferably planar, solid ion-selective electrodes 14, 14' (hereinafter, "ISE's"). The ISE's are preferably adhered to exterior surface 13 of device 10 by an adhesive, formed in a layer 15, FIG. 2. As described in U.S. Pat. No. 4,053,381, issued on Oct. 11, 1977, the details of which are expressly incorporated herein by reference, each ISE is a generally flat multilayered element comprising adjacent layers 16–20. (The layer thicknesses are exaggerated in FIG. 2 for clarity.) Each layer 16 is an ion-selective membrane containing an ionophore and a solvent. When a drop of sample liquid or reference fluid makes contact, the ion of choice is carried by or otherwise effectively penetrates through layer 16 to the underlying layers 17–18. At these layers, an electrical potential is generated proportional to the activity of that particular ion. Layer 17, for example, is a dried hydrophilic binder containing the salt $X^{\oplus}Z^{\ominus}$, where $X^{\oplus}$ is the analyte to be measured. Layer 18 in such instances is the $Z^{\ominus}$ salt of an electrically conductive metal $M^{61}$, and metal $M°$ forms layer 19. Layer 20 is an insulative support. Because layers 18 and 19 are electrically conductive layers, a potential can be detected by an electrometer, not shown, via probes which penetrate through layer 18 into contact with layer 19 at windows 22 in frame 12, FIG. 1. Any difference in these potentials due to two different ionic activities of the ion of choice in the two liquids is registered as a difference potential on the electrometer. This reading then is converted into a measure of concentration of the ionic analyte.

Useful embodiments include those in which one or more of layers 16–19 are altered, omitted, or added to. For example, if ISE 14 is constructed to test for $Cl^{\ominus}$, the laminated layers are as follows: a polyethylene terephthalate support, and a layer thereon of $Ag°$ over which a layer of silver chloride is formed. A top layer of cellulose acetate, containing a surfactant and polyethylene glycol, is added as described in U.S. Pat. No. 4,199,411, issued on Apr. 27, 1980, for the purpose of removing bromide interference.

Figure 2:
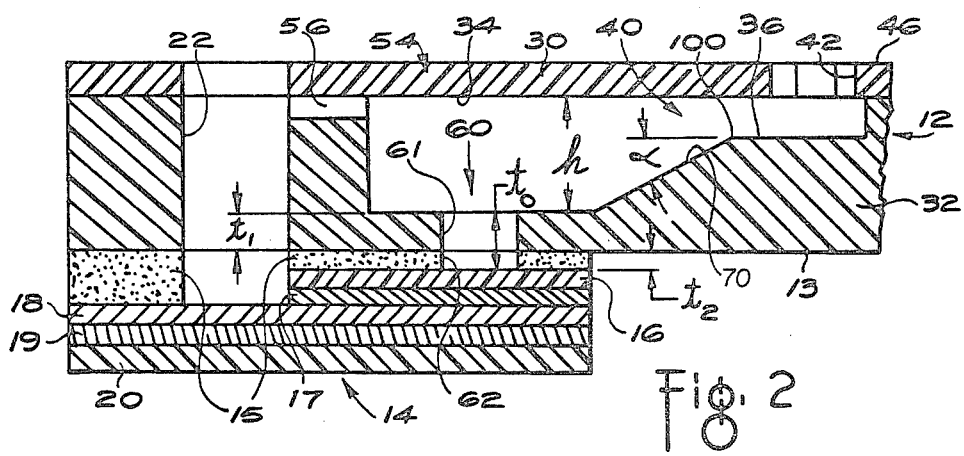
FIG. 2 is a fragmentary section view taken generally along the line II—II of FIG. 1.

Frame 12 is formed by a pair of members 30 and 32, FIG. 2, having opposing internal surfaces 34 and 36, respectively, forming transport surfaces for the liquids. Member 30 has an exterior surface 46. Surfaces 34 and 36 are spaced apart a distance effective to provide capillary flow of introduced liquid and to form a capillary transport zone 40, in the manner described in U.S. Pat. No. 4,302,313. The contents of that patent are expressly incorporated herein by reference. The capillary spacing providing the capillary flow is preferably no greater than about 600 microns.

In addition to the opposing surfaces 34 and 36, zone 40 is further defined by flow-terminating means, which most preferably comprise sidewalls 41 and 43, FIG. 1, past which the liquid flows. The flow-through width of zone 40 is measured between these sidewalls. Alternatively, an exposed edge will act as a flow-terminating means, as is described in my U.S. Pat. No. 4,254,083, col. 3. Such an edge is obtainable by vertically slicing the device 10, FIG. 1, along a plane coinciding with the plane of outer walls 43, to provide a flow-terminating means that defines flow-through width w.

Figure 3:
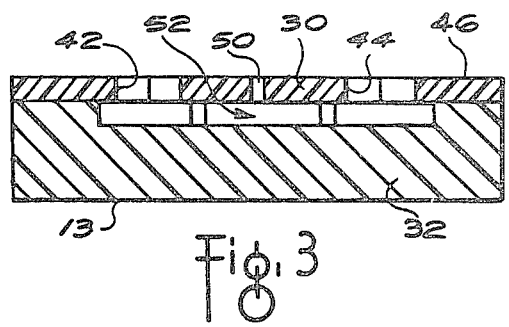
FIG. 3 is a section view taken generally along the line III—III of FIG. 1.

To admit the two liquids into zone 40, access apertures 42 and 44, FIGS. 1–3, are formed in member 30. These apertures preferably have a shape that includes at least one corner to insure that a drop of liquid deposited by a metering device, not shown, on exterior surface 46, FIG. 2, approximately at one of the apertures, will enter the aperture and thus zone 40. Most preferably, the apertures are shaped for this purpose in the manner described in U.S. Pat. No. 4,254,083, issued Mar. 3, 1981. The contents of the '083 patent are expressly incorporated herein by reference. As shown in FIG. 1, a hexagon is a particularly useful flow-through shape for apertures 42 and 44.

To vent entrapped air from zone 40 as the two liquids move toward each other, one or more apertures 50, FIGS. 1 and 3, are formed in member 30, approximately centered between apertures 42 and 44. Apertures 50 are much smaller, e.g., 1 mm or less, than apertures 42 and 44 because they do not need the volume capability of the latter.

Thus, zone 40 transports the liquids towards each other in the portion 52, FIGS. 1 and 3, extending between apertures 42 and 44. When the liquids contact each other in the vicinity of apertures 50, they form an ion bridge, the first part of the ionic circuit needed for ion measurement by the electrometer.

Arm portions 54 of zone 40 extend from bridge portion 52, thus giving to zone 40 a horseshoe shape. The flow-through width of each arm portion 54 is designated as having a value "w", FIG. 1. The two liquids are carried towards ISE's 14 and 14' by such arm portions. To allow venting of air entrapped ahead of liquid advancing along arm portions 54, an air vent 56, FIG. 2, is provided, fluidly connecting each arm of zone 40 with a window 22. Vent 56 preferably has a greatly reduced flow-through diameter, for example, 75 microns or less, to minimize gas-liquid interchange in the liquid under test. For example, if the ISE's 14 and 14' are chosen to test for $CO_2$ (or $HCO_3^{\ominus}$), then it is undesirable that a large surface area of the liquid should be exposed to the air. To this end, zone 40 is sealed along the edges and is "vented" only at vents 50 and 56 and access apertures 42 and 44.

A second zone of capillary transport is provided commencing with a diverting aperture 60, FIG. 2, formed by sidewalls 61 that extend from surface 36 of member 32 to exterior surface 13. Sidewalls 61 generally provide a flow-through width dimension and a flow-through length dimension. In the case of circular embodiments as shown, such dimensions are equal and comprise the diameter. In addition, aperture 60 includes a dimension (diameter) that extends in a direction that parallels width w of zone portion 54. Aperture 60 is most preferably centered between sidewalls 41 and 43 and is fluidly connected to an aperture 62 formed in and surrounded by adhesive layer 15, and layer 16 provides the terminating surface of the second zone. Thus, the second zone extends from a first end that is the intersection of sidewalls 61 with surface 36, to the surface of layer 16 exposed by aperture 62 in the adhesive layer. The length of such zone is the distance the liquid must flow in the second zone for the intended use, and it is the distance $t_o$ equal to the sum of $t_1$ and $t_2$. Thickness $t_1$ is the thickness of member 32 at aperture 60 and $t_2$ is the thickness of adhesive layer 15 at aperture 62 (the distance between surface 13 of member 32 and the surface of layer 16). To insure adequate contact with the ISE's at layer 16, the flow-through area of apertures 60 and 62 is greater than about 0.2 mm$^2$.

The second zone is sealed, with no air vent being present in the second zone. Such second zone air vents are disadvantageous for several reasons. First, they tend to render non-constant the area of contact of liquid on the terminating surface of the second zone. If the terminating surface is an ISE, a non-constant area interferes with the maintenance of a constant signal. Second, the air vents tend to cause a change in concentration of certain ions, such as $HCO_3^{63}$, and to cause leakage of the liquid, producing contamination. Third, the air vents complicate the design and assembly unnecessarily.

Figure 4:
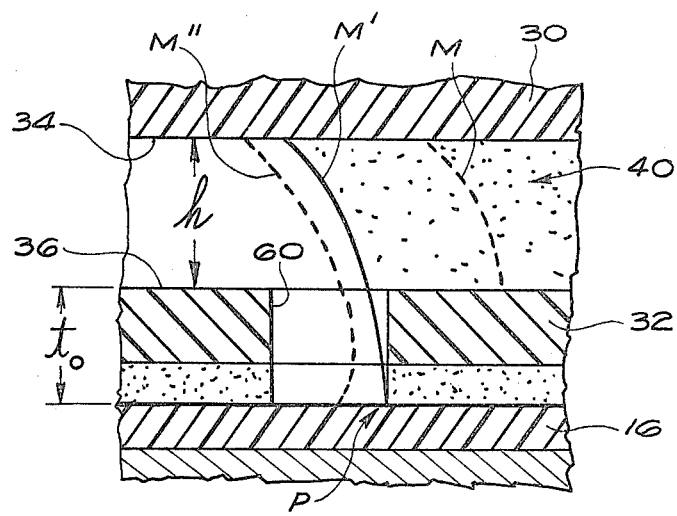
FIG. 4 is a fragmentary section view similar to that of FIG. 2, except considerably enlarged.

In accordance with one aspect of the invention, adequate flow of liquid to the terminal surface of layer 16 occurs if the proper value of liquid head h is selected for a given value of $t_o$, and the proper first zone width w is selected for the parallel dimension of the aperture. That is, for a given set of conditions, the head h is an empirically determinable function of $t_o$. This function appears to be dependent on the surface tension of the liquid flowing in the device, the contact angle that liquid forms with the materials comprising the members of the first zone, and the relative value of the flow-through width of the diverting aperture, compared to the flow-through width of the first zone at that aperture. The exact expression of the function and the mechanism causing it are not completely understood for all conditions, although a specific embodiment is hereinafter described. The mechanism appears to be that schematically illustrated in FIG. 4. In the illustrated embodiment, member 30 is selected with a surface 34 that is a readily wettable material having a contact angle for serum between about 60° and 80°, although materials having lower contact angles, even those approaching 0°, are acceptable. Member 32, on the other hand, has a surface 36 that is a relatively non-wettable material, with a contact angle greater than or equal to 85°. In such a case, the meniscus M advances from its right-hand position, shown in zone 40 in dashed lines, generally with the shape shown, until it encounters aperture 60. If h is sufficiently large for a given $t_o$, and the flow-through widths are properly selected as described hereinafter, the meniscus continues to advance to the position M', shown in solid lines. At this stage, the liquid contacts the surface of layer 16, e.g., at point P, before the liquid completely surrounds aperture 60 in its continued flow in zone 40. If all other factors are held constant, the greater the distance $t_o$, the greater the value h must be to provide the energy that insures this contact with layer 16 will occur before the liquid flow in zone 40 surrounds the aperture. (As noted in the "Background", flow in the first zone that surrounds the diverting aperture is to be avoided before liquid contact is made with the terminating surface of layer 16. It has been found that it is difficult to fill the second zone once the diverting aperture is so surrounded, because of air entrapment.)

Once contact is achieved with the surface of layer 16, the meniscus moves on, as shown by the dashed line M", to fill up second zone.

The same mechanism is effective, to produce substantially the same results, if the contact angles for surfaces 34 and 36 are reversed. In such a case, meniscus M advances with the bottom edge leading the top (not shown), until aperture 60 is reached, FIG. 4. The energy barrier of the aperture acts to "pin" the bottom edge of the meniscus while the top edge moves forward until the meniscus is approximately in position M'. Thereafter, filling of the second zone occurs as in the previously described embodiment. However, the ability of the liquid to wet a given material for members 30 and 32 will tend to alter how much head h is needed for a given thickness $t_o$, as will the surface tension of the liquid. For example, the greater the wettability of surface 34 compared to surface 36, the more the meniscus edge at surface 34 "leads" its edge at surface 36. The greater this disparity, the greater the pressure that the head h tends to apply, and the greater the distance that is useful for $t_o$. Furthermore, the value of h for a given thickness $t_o$ also depends on the resistance to first zone flow provided by the diverting aperture. If the width w of zone portion 54, FIG. 1, is much greater than the flow-through dimension (width or length) of aperture 60 that is parallel to w, the liquid will act as though the aperture were not there, and surround aperture 60 before it contacts layer 16. On the other hand, if the flow-through width of the first zone only equals the parallel dimension of the diverting aperture, the resistance to flow into the diverting aperture is increased to the point where the device is inoperative. More specifically, if aperture 60 is, for example, rectangular with a flow-through length extending parallel to the width w of the first zone, and is dimensioned to equal that width w, liquid flow in zone 40 will not readily proceed into aperture 60.

Therefore, the resistance to first zone flow created by the diverting aperture, the advancing contact angles for the materials used, and the liquid surface tension must be considered in determining the value of h for a given $t_o$.

For one preferred embodiment of this invention, the surface of member 30 is selected from materials that provide a contact angle, for the liquid to be used, of between about 60° and about 80°, as described above in connection with FIG. 4. The ratio of width w of zone 40 to the parallel dimension of aperture 60 is between about 1.1 to 1 and about 1.5 to 1. Stated reversely, the parallel dimension of the diverting aperture is between about 0.65 and about 0.9 of the first zone flow-through width. Care is taken to center aperture 60 between sidewalls 41 and 43, as otherwise the range of ratios noted above for the parallel dimension of the aperture and the first flow-through width will not accurately reflect the conditions needed for proper flow. More specifically, insufficient clearance of the aperture along one wall and a large clearance at the opposite sidewall permits liquid to flow past the aperture through the large clearance, and the aperture becomes surrounded by the liquid. Finally, the terminating surface of layer 16 is selected so as to have an advancing contact angle less than about 85°, and a receding contact angle no greater than about 30°, to prevent the liquid from de-wetting at point P. De-wetting tends to lead to aperture 60 becoming surrounded and air being entrapped in the second zone.

Thus, particularly preferred devices include those in which at least surface 34 of member 30 is triacetate, at least surface 36 of member 32 is polystyrene, aperture 60 is circular, the ratio of width w to the diameter of aperture 60 is about 1.28 to 1.0, and layer 16 is a cellulose acetate overcoat of a chloride electrode as described in the aforesaid U.S. Pat. No. 4,199,411. Preferred diameters of aperture 60, in such embodiments, range between about 2.0 mm and about 5.0 mm, provided that the width w of zone 40 is modified to provide the 1.28 to 1 ratio noted above. For such an embodiment, as will be seen in the examples that follow, the relationship between h and $t_o$ such that satisfactory wetting of the ISE occurs, is $h \geq 150 + 0.87 t_o$, measured in microns. Since it is desired that, for good capillary flow, h should not exceed about 600 $\mu$, then $t_o$ in such an embodiment does not exceed about 515 $\mu$.

Thus it will be apparent that the present device provides more reliable flow over a longer path length than was suggested for use in the device of my aforesaid U.S. Pat. No. 4,271,119, absent an air vent in the second zone.

The second zone need not terminate with the surface of layer 16 adhered directly to member 32, in order that the diverting aperture 60 should function as described. That is, useful embodiments include those in which the terminating surface of the second zone is spaced a short distance from the apertured member 32 by an intervening wall member, as shown for example in FIG. 2 of my aforesaid patent.

The fluid height h of zone 40 at aperture 60 is a useful capillary spacing throughout zone 40. However, to conserve the volume of liquid required to fill zone 40, those portions of zone 40 removed from the location of aperture 60 are preferably decreased in their capillary spacing. An additional advantage of such a construction is that it permits member 32 to be thicker at portions removed from aperture 60, for ease in manufacturing.

Thus, bridge portion 52 has a spacing between surfaces 34 and 36 that is less than distance or height h. However, that distance is increased by reason of ramp 70, ramp 70 being preferably inclined at an angle α of less than 30°, FIG. 2, until the value of h is reached as advancing liquid approaches aperture 60. Angle α is selected to be small to avoid creating an energy barrier at 100 to the flow of liquid.

The invention has been described in connection with diverting apertures 60 that are circular. It will be readily apparent that non-circularly shaped apertures are also useful with the invention. Thus, a square flow-through shape is also useful, as are the shapes described in my aforesaid U.S. Pat. No. 4,271,119.

Examples 1-3

A first capillary transport zone was provided by two spaced-apart members wherein the bottom member was a sheet of polystyrene apertured with a circular punch that was about 2.5 mm in diameter. The top member was triacetate and the width w of the first zone at the diverting aperture was about 3.2 mm. To create the second zone, the apertured member was adhered, at the aperture, to a Cl⊖ ISE as described above, using a layer of GELVA adhesive that was about 25.4 microns thick. To vary the fluid height above the aperture and the thickness of the second zone, the thicknesses of (a) the spacer separating the opposed surfaces of the first zone and of (b) the bottom member, were varied as set forth in the following Table I:

TABLE I

| Example | Spacer Thickness (h)* | Thickness of Bottom Member* | Total Thickness Second Zone($t_o$)* |
|---|---|---|---|
| 1 | 229μ | 25.4μ | 51μ |
| 2 | 254μ | 76μ | 102μ |
| 3 | 203μ | 25.4μ | 51μ |
| Comp. Ex. 1 | 229μ | 102μ | 127μ |
| Comp. Ex. 2 | 178μ | 25.4μ | 51μ |

*These thicknesses were determined by selecting thicknesses measured as mils of an inch, and by converting to rounded off metric units.

To determine whether liquid would flow into the punched aperture, 5 ml of human serum or water was used as the liquid, each being spiked with 100 μl of a fluorescent composition comprising europium imbibed in a styrene-acrylamide methacrylic acid latex, for enhanced visual observation. (Other fluorescent materials also are useful.) In addition, the ISE was connected, at the portion corresponsing to the exposed surface at window 22 of FIG. 2, to a voltmeter set at the 10Kohm setting. The other probe of the voltmeter was immersed in the liquid that was supplied to the first capillary zone. When and only when liquid filled the second zone comprising the circular aperture, the voltmeter went off scale.

The results appear in Table II.

TABLE II

| Example | Liquid Tested | Flow Successfully Diverted? |
|---|---|---|
| 1 | serum | Yes |
| 2 | serum | Yes |
| 3 | serum | Yes |
| Comp. Ex. 1 | serum | No |
| Comp. Ex. 2 | water | No |

Examples 4 and 5

The procedure of Example 1 was repeated except h was selected to equal about 305 μ and about 330 μ, respectively. Total thickness $t_o$ was equal to 178 μ in both cases, by using a bottom member having a thickness of about 102 μ and a 25.4 μ thick tape having adhesive on both sides. The thickness of the adhesive on each side was about 25.4 μ. In both Examples 4 and 5, satisfactory flow of serum into the second zone and wetting of the electrode were observed.

Example 6

The procedure of Examples 1-3 was repeated, using spiked serum, and the terminating surface for the second zone (under the circular aperture) was glass instead of the Cl⊖ISE. No voltmeter was used to determine diversion of flow. As a control, the thicknesses were selected to give h=229 μ and $t_o$=127 μ. Diversion of flow did not occur, as determined visually. However, when this experiment was repeated (Example 6) with a thickness $t_o$ equal to only 76 μ, diversion of capillary flow did occur.

Figure 5:
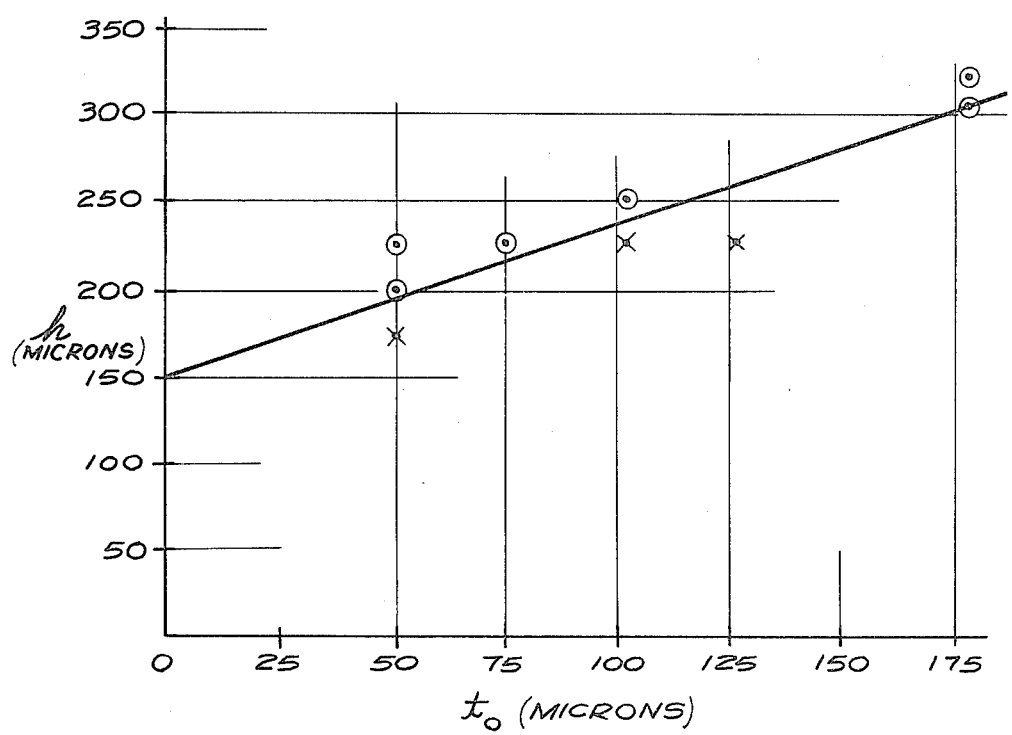
FIG. 5 is a graph of liquid head h at the diverting aperture, plotted against second zone lengths $t_o$, measured in microns, for a preferred embodiment.

The values for h and $t_o$ used in Examples 1-6 were plotted in the graph of FIG. 5. Those values that provided successful flow to the terminating surface of the second zone are marked with circles, and those comparative examples that failed with "x's." As is apparent, the data indicates a linear division between successful flow and unsuccessful flow, which division approximately follows the equation $$h = 150 + 0.87 t_o, \text{ measured in microns.} \quad (1)$$

Thus, if for the device described in Example 1, h equals or exceeds the value predicted by equation (1), the liquid introduced into the first zone also flows into the second zone and wets the ISE, without the need for an air vent in the second zone.

The invention has been described in detail with particular reference to preferred embodiments thereof, but it will be understood that variations and modifications can be effected within the spirit and scope of the invention.

What is claimed is:

1. A liquid transport device comprising
means defining a first capillary transport zone, said means including (i) a first set of opposing surfaces spaced apart a distance effective to provide capillary flow of introduced liquid, and (ii) flow-terminating means defining a flow-through width of said first zone;
liquid access means for admitting liquid into said first zone;
means for venting air entrapped in said first zone; and means defining a second, non-vented capillary transport zone having two spaced-apart ends, including:
(a) means defining, at one of said ends and in one of said opposing surfaces, a diverting aperture located downstream from said access means and having (1) a width dimension which is greater than 0.4 of its length dimension, (2) a dimension extending parallel to said first zone flow-through width that is between about 0.65 and about 0.9 of the said flow-through width, and (3) a flow-through area greater than about 0.2 mm$^2$; and
(b) a terminating surface disposed at the other of said ends of said second zone opposite said diverting aperture;
the relationship of (i) the spaced-apart distance between said opposing first zone surfaces at said diverting aperture, to (ii) the distance between said opposing surface containing said diverting aperture and said terminating surface, being effective to insure that the liquid of said first zone enters said diverting aperture and contacts said terminating surface, before the flow of the liquid in said first zone surrounds said diverting aperture,
whereby liquid flows to said terminating surface in response to capillary force even in the absence of venting means in said second zone.

2. A device as defined in claim 1, wherein at least one of said members is readily wetted by a liquid having a surface tension between about 25 and about 75 dynes/cm.

3. A device as defined in claim 1, wherein the surface of said first zone opposite to said diverting aperture is made of a material which forms a contact angle with said liquid of between about 60° and about 80°.

4. A device as defined in claim 2 or 3, wherein said spaced-apart distance is at least that defined by the equation $$h = 150 + 0.87 t_o$$

wherein h is said spaced-apart distance and $t_o$ is said distance of said second zone between said opposing surface and said terminating surface, in microns.

5. A device as defined in claim 1 or 2, wherein said diverting aperture is circular in shape.

6. A device as defined in claim 1 or 2, wherein a portion of said terminating surface is adhered to said opposing surface containing said diverting aperture.

7. A device as defined in claim 6, wherein said terminating surface is an exterior surface of an ion-selective electrode.

8. A device as defined in claim 7, wherein said ion-selective electrode comprises layers of materials adapted to assay for Cl$^\ominus$.

9. A device as defined in claim 1 or 2, wherein said spaced-apart distance at said first zone is less, at locations distal to said diverting aperture, than said spaced-apart distance at said diverting aperture, whereby the total amount of liquid required to fill said first zone is reduced.

10. A liquid transport device comprising
means defining a first capillary transport zone, said means including (i) a pair of members having a first set of opposing surfaces spaced apart a distance effective to provide capillary flow of introduced liquid, and (ii) flow-terminating means defining a flow-through width of said first zone;
liquid access means for admitting liquid into said first zone;
means for venting entrapped air in said first zone; and
means defining a second, non-vented capillary transport zone having two spaced-apart ends, including:
(a) means defining, at one of said ends and in the opposing surface of one of said members, a diverting aperture located downstream from said access means and having (1) a width dimension which is greater than 0.4 of its length dimension, and (2) a transverse cross-section flow-through area greater than about 0.2 mm$^2$; and
(b) a terminating surface disposed at the other of said ends of said second zone opposite said diverting aperture;
the relationship of the spaced-apart distance between said opposing first zone surfaces at said diverting aperture, to the distance between said opposing surface containing said diverting aperture, and said terminating surface, and the relationship of said width of said first zone at said diverting aperture, to the dimension of said diverting aperture that extends parallel to said first zone flow-through width, being effective to insure that the liquid of said first zone enters said diverting aperture and second zone and contacts said terminating surface, before the flow of the liquid in said first zone surrounds said diverting aperture,
whereby liquid flows under capillary forces to said terminating surface even in the absence of venting means in said second zone.

11. A device as defined in claim 10, wherein at least one of said members is readily wetted by a liquid having a surface tension between about 25 and about 75 dynes/cm.

12. A device as defined in claim 10 or 11, wherein said diverting aperture is circular in shape.

* * * * *